United States Patent [19]
Pehu et al.

[11] Patent Number: 5,851,953
[45] Date of Patent: Dec. 22, 1998

[54] YIELD OF PLANTS

[75] Inventors: Eija Pehu; Erkki Virtanen, both of Helsinki; Kirsti Jutila, Espoo, all of Finland

[73] Assignee: Cultor OY, Finland

[21] Appl. No.: 793,737

[22] PCT Filed: Sep. 7, 1995

[86] PCT No.: PCT/FI95/00482

§ 371 Date: Apr. 11, 1997

§ 102(e) Date: Apr. 11, 1997

[87] PCT Pub. No.: WO96/41531

PCT Pub. Date: Dec. 27, 1996

[30] Foreign Application Priority Data

Jun. 9, 1995 [FI] Finland ..................... 952864

[51] Int. Cl.⁶ .......................... A01N 37/00; A01N 37/02; A01N 37/30
[52] U.S. Cl. .......................... 504/320; 504/345; 514/556
[58] Field of Search ..................... 504/345, 320; 514/556

[56] References Cited

FOREIGN PATENT DOCUMENTS 0 181 494  5/1986  European Pat. Off. .
WO 9535022  12/1995  WIPO .

OTHER PUBLICATIONS

Label, Miller GREENSTIM™ Liquid Fertilizer, a product of the U.K., manufactured for Miller Chemical & Fertilizer Corporation, Hanover, Pennsylvania (1992).

Hofinger et al Dept. of Gen. Biology, Institute Van Beneden, pp. 303–309 "Assigning a Biological Role to Hypaphorine and Lycine (Two Betaines)".

Åberg Swedish J. Agric. Res. 12:51–61, 1982 "Plant Growth Regulators".

STN International, File WPIDS, WPIDS, accession. No. 89–312201, Chikkarin K: "Pant supported on basal be –is cultivated with nourishing liq. Contg. Betaine (s)"; & JP, A, 01228416, 890912(8943).

Journal of Experimental Botany, vol. 38, No. 188, Mar. 1987, M.I. Lone et al, "Influence of Proline and Glycine-betaine on Salt Tolerance of Cultured Barley Embryos" pp. 479–490.

Plant Science Letters, vol. 25, 1982, C. Itai et al, "Responses of Water–Stressed *Hordeum distichum* L. And *Cucmis sativus* to Proline and Betaine" pp. 219–335.

J. Plant Physiol., vol. 140, 1992, Y Zhao et al, "Protection of Membrane Integrity in *Medicago sativa* L. By Glyci-negetaine against the Effects of Freezing" pp. 541–543.

Patent Abstracts of Japan, vol. 13, No. 516, C–656, abstract of JP, A, 1–208386 (Katakura Chitsukarin K.K.) 22 Aug. 1989.

*Primary Examiner*—Allen J. Robinson
*Attorney, Agent, or Firm*—Nixon & Vanderhye

[57] ABSTRACT

Exogenous use of betaine on tobacco plants improves the yield, especially tobacco plants grown under stress conditions.

8 Claims, No Drawings

YIELD OF PLANTS

This application is a 371 of PCT/FI95/00482 filed Sep. 7, 1995.

TECHNICAL FIELD

The invention relates to the use of betaine to improve the yield of plants. The invention relates especially to the use of betaine to improve the yield of tobacco plants (*Nicotiana spp.*). According to the invention, the yield can be improved particularly under stress conditions, i.e. when the conditions are poor due to e.g. drought, high salinity, low temperatures, a humidity or environmental poisons interfering with the growth. The invention also relates to tobacco plants treated with betaine, to tobacco leaves and other parts of a tobacco plant, and to products prepared from these.

BACKGROUND

The environment and conditions of growth considerably affect the yield of plants. Optimum growth environment and conditions usually result in a yield that is large in quantity and high in quality. Under poor growth conditions both the quality and the quantity naturally deteriorate.

The physiological properties of a plant are manipulated by means of breeding, both with traditional breeding methods and for example with genetic manipulation.

Several different solutions concerning cultivation technique have been developed to improve the growth conditions and yield of plants. Selecting the right plant for the right growth location is self-evident for a person skilled in the art. During the growing season plants may be protected with mechanical means by utilizing for example different gauzes or plastics or by cultivating the plants in greenhouses. Irrigation and fertilizers are generally used in order to improve the growth. Surfactants are often used in connection with applying pesticides, protective agents and minerals. Surfactants improve the penetration of substances to plant cells, thereby enhancing and increasing the effect of the aforementioned agents and simultaneously reducing their harmful effects on the environment. However, different methods of cultivation technique are often laborious and impractical, their effect is limited (the economical size of a greenhouse, the limited protection provided by gauzes, etc.), and they are also far too expensive on a global scale. No economically acceptable chemical solutions for protecting plants from environmental stress conditions have been described so far.

Water supply is more important than any other environmental factor for the productivity of a crop. Irrigation is usually utilized to ensure sufficient water supply. However, there are significant health and environmental problems related to irrigation, for example a sharp decrease in water resources, deterioration of water quality and deterioration of agricultural lands. It has been calculated in the field that about half of the artificially irrigated lands of the world are damaged by waterlogging and salinization. An indication of the significance and scope of the problem is that there are 255 million hectares of irrigated land in the world, and they account for 70% of the total world water consumption. In the United States alone, there are over 20 million hectares of irrigated land mainly in the area of the 18 western states and in the southeastern part of the country. They use 83% of the total water consumption for irrigation alone. It can also be noted that the use of irrigation water increases every year especially in industrial countries. In addition to these problems, another drawback of irrigation is the high cost.

The productivity of plants in dry conditions, i.e. the sensitivity of crops to drought, varies according to the plant variety. Crop species, such as tobacco (*Nicotiana spp.*), that produce fresh leaves are highly sensitive to drought, and they cannot be produced commercially in areas or during seasons with a limited water supply and a high degree of evaporation.

Another serious stress factor is the salinity of soil. The salinity of soil can be defined in different ways; according to the general definition, soil is saline if it contains soluble salts in an amount sufficient to interfere with the. growth and yield of several cultivated plant species. The most common of the salts is sodium chloride, but other salts also occur in varying combinations depending on the origin of the saline water and on the solubility of the salts.

It is difficult for plants growing in saline soil to obtain a sufficient amount of water from the soil having a negative osmotic potential. High concentrations of sodium and chloride ions are poisonous to plants. An additional problem is the lack of minerals, which occurs when sodium ions compete with potassium ions required, however, for cell growth, osmoregulation and pH stabilization. This problem occurs especially when the calcium ion concentration is low.

The productivity of plants and their sensitivity to the salinity of soil also depend on the plant species. Halophytes require relatively high sodium chloride contents to ensure optimum growth, whereas glycophytes have low salt tolerance or their growth is considerably inhibited already at low salt concentrations. There are great differences even between different cultivars of a cultivated plant species. The salt tolerance of one and the same species or cultivar may also vary depending for example on the stage of growth. In the case of low or moderate salinity, the slower growth of glycophytes cannot be detected in the form of specific symptoms, such as chlorosis, but it is shown in the stunted growth of the plants and in the colour of their leaves that is darker than normal. Moreover, the total leaf area is reduced, carbon dioxide assimilation decreases and protein synthesis is inhibited.

Plants can adapt to some extent to stress conditions. This ability varies considerably depending on the plant species. As a result of the aforementioned stress conditions, certain plants begin to produce a growth hormone called abscisic acid (ABA), which helps the plants to close their stomata, thus reducing the severity of stress. However, ABA also has harmful side effects on the productivity of plants. ABA causes for example leaf, flower and young fruit drop and inhibits the formation of new leaves, which naturally leads to reduction in yield.

Stress conditions and especially lack of water have also been found to lead to a sharp decrease in the activity of certain enzymes, such as nitrate reductase and phenylalanine ammonium lyase. On the other hand, the activity of alpha-amylase and ribonuclease increases. No chemical solutions, based on these findings, to protect plants have been described so far.

It has also been found that under stress conditions certain nitrogen compounds and amino acids, such as proline and betaine, are accumulated in the regions of growth of certain plants. The literature of the art discusses the function and meaning of these accumulated products. On the one hand it has been proposed that the products are by-products of stress and thus harmful to the cells, on the other hand it has been estimated that they may protect the cells (Wyn Jones, R. G. and Storey, R.: *The Physiology and Biochemistry of Drought Resistance in Plants*, Paleg, L. G. and Aspinall, D. (Eds.), Academic Press, Sydney, Australia, 1981).

Zhao et al. (in *J. Plant Physiol.* 140 (1992) 541–543) describe the effect of betaine on the cell membranes of alfalfa. Alfalfa seedlings were sprayed with 0.2M glycinebetaine, whereafter the seedlings were uprooted from the substrate, washed free of soil and exposed to temperatures from −10° C. to −2° C. for one hour. The seedlings were then thawed and planted in moist sand for one week at which time regrowth was apparent on those plants that had survived. Glycinebetaine clearly improved the cold stability of alfalfa. The effect was particularly apparent at −6° C. for the cold treatment. All controls held at −6° C. for one hour died, whereas 67% of the seedlings treated with glycinebetaine survived.

Itai and Paleg (in *Plant Science Letters* 25 (1982) 329–335) describe the effect of proline and betaine on the recovery of water-stressed barley and cucumber. The plants were grown in washed sand, and polyethylene glycol (PEG, 4000 mol. wt.) was added to the nutrient solution for four days in order to produce water stress, whereafter the plants were allowed to recover for four days before harvesting. Proline and/or betaine (25 mM, pH 6.2) was sprayed on the leaves of the plant either on the first or third day of the stress or immediately before harvesting. As regards barley, it was noted that betaine supplied either before or after the stress had no effect, whereas betaine added in the end of the stress was effective. Proline had no effect. No positive effect was apparent for cucumber. On the contrary, it was found out that both betaine and proline had a negative effect.

Experiments aiming at clarifying the effects of betaine and proline on plants have thus yielded contradictory results, and there are no commercial applications based on these results.

BRIEF DESCRIPTION OF THE INVENTION

The purpose of the present invention was to find a way to partially replace artificial irrigation so that the amount and quality of the yield could be simultaneously ensured. Another purpose of the invention was to find a way to protect plants also under other stress conditions, such as during high salinity often connected with drought, at low temperatures, etc. Moreover, a further aim was to find a way to increase the yield under normal conditions without utilizing methods that would consume environmental resources or harm the environment.

In connection with the present invention it has now surprisingly been found that the yield of tobacco plants, for example the amount and quality of the yield, can be considerably improved by means of betaine that is applied exogenously. Betaine has been found to be especially effective in improving the yield under stress conditions, and it has no such detrimental effects as the side effects of ABA.

The invention thus relates to the exogenous use of betaine to improve the yield of tobacco plants. According to the invention, betaine is used exogenously to improve the yield of plants under both normal and stress conditions.

The invention also relates to tobacco leaves of tobacco plants treated exogenously with betaine, and to the use of the leaves in products of tobacco industry.

The invention also relates to a method of improving the yield of tobacco plants, in which method betaine is exogenously applied to growing tobacco plants.

Betaine is applied to the plant in either one or several successive treatments. The application may be performed for example by spraying together with for example a fertilizer, if desired. Betaine used according to. the invention is transported to plant cells, where it actively regulates the osmotic balance of the cells and also participates in other processes of cell metabolism. A plant cell treated with betaine is more viable even when subjected to exogenous stress factors.

The betaine treatment according to the invention is economically advantageous, and the yield increases in an amount that is economically profitable and significant. The treatment does not produce significantly more work since it may be performed together with other sprayings, and it does not require new investments in machinery, equipment or space. It should also be noted that betaine is a non-toxic natural product, which has no detrimental effects on the quality of the yield. Betaine is also a stable substance that remains in the plant cells and thereby has a long-standing effect.

DETAILED DESCRIPTION OF THE INVENTION

Betaine refers to fully N-methylated amino acids. Betaines are natural products that have an important function in the metabolism of both plants and animals. One of the most common betaines is a glycine derivative wherein three methyl groups are attached to the nitrogen atom of the glycine molecule. This betaine compound is usually called betaine, glycinebetaine or trimethylglycine, and its structural formula is presented below:

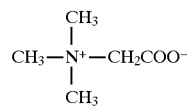

Other betaines are for example alaninebetaine and prolinebetaine, which has been reported to for example prevent perosis in chicks. R. G. Wyn Jones and R. Storey describe betaines in detail in *The Physiology and Biochemistry of Drought Resistance in Plants* (Paleg, L. G. and Aspinall, D. (Eds.), Academic Press, Sydney, Australia, 1981). The reference is included herein by reference.

Betaine has a bipolar structure and it contains several chemically reactive methyl groups which it can donate in enzyme-catalyzed reactions. Most organisms can synthesize small amounts of betaine for example for the methyl function, but they cannot react to stress by substantially increasing the production and storage of betaine. Best known organisms accumulating betaine are plants belonging to the Chenopodiaceae family, for example sugar beet, and some microbes and marine invertebrates. The main reason for the betaine accumulation in these organisms is probably that betaine acts as an osmolyte and thus protects the cells from the effects of osmotic stress. One of the main functions of betaine in these plants and microbes is to increase the osmotic strength of the cells when the conditions require this, for example in case of high salinity or drought, thus preventing water loss. Unlike many salts, betaine is highly compatible with enzymes, and the betaine content in cells and cell organelles may therefore be high without having any detrimental effect on the metabolism. Betaine has also been found to have a stabilizing effect on the operation of macromolecules; it improves the heat resistance and ionic tolerance of enzymes and cell membranes. Tobacco plants do not normally store betaine in their cells.

Betaine can be recovered for example from sugar beet with chromatographic methods. Betaine is commercially available from Cultor Oy, Finnsugar Bioproducts as a product that is crystalline water-free betaine. Other betaine products, such as betaine monohydrate, betaine hydrochloride and raw betaine liquids, are also commercially available and they can be used for the purposes of the present invention.

According to the present invention, betaine is thus used exogenously to improve the yield of tobacco plants. According to the invention, betaine is used to improve the yield of tobacco plants especially under stress conditions, i.e. when the plants are subjected to periodic or continuous exogenous stress. Such exogenous stress factors include for example drought, high temperatures, high salinity, herbicides, environmental poisons, etc. Treating plants subjected to stress conditions exogenously with betaine for example improves the adaptation of the plants to the conditions and maintains their growth potential longer, thereby improving the yield-producing capacity of the plants. Betaine is also a stable substance that remains in the plant cells. The positive effect of betaine is thereby long-standing and diminishes only gradually due to dilution caused by the growth.

Even though this reference and the claims use the word 'betaine', it is clear that according to the invention several different betaines can be used. It should also be noted that betaine is used here as a general term which thus covers different known betaines.

Betaine is applied to tobacco plants in either one or several successive treatments. Application in a single dose is considered preferable. The amount used varies depending on the tobacco cultivar and the stage of growth. A useful amount may be for example about 0.2 to 40 kg of betaine per hectare. A preferable amount is thus for example about 3 to 9 kg of betaine per hectare. The amounts given here are only suggestive; the scope of the present invention thus contains all amounts that work in the manner described herein.

Any method suitable for the purpose may be used to apply betaine. Betaine can be applied separately or together with other plant protectants, pesticides or nutrients, such as fungicides and urea or micronutrients. Betaine can be applied easily for example by spraying. Foliar application of betaine and possible other agents through spraying is a preferable method which enables a more rapid response than methods involving root application. However, there may be different problems related to this method, such as low penetration concentrations in leaves with thick cuticles, run-off from hydrophobic surfaces, washing off by rain, rapid drying of the solution and leaf damage. In order to avoid these problems it is worthwhile to consider using also other methods to apply betaine.

According to the invention, betaine is preferably used in the form of an aqueous solution.

The time of the treatment according to the invention may also vary. If betaine is applied in a single treatment, the treatment is usually performed at an early stage of growth, for example when the leaves have just come out. If betaine is applied in several successive treatments, a new spraying is performed preferably in the beginning of flowering or when stress can be forecasted on the basis of the weather.

The betaine treatment according to the invention considerably improves the yield of tobacco plants, for example the amount and quality of the yield. The treatment according to the invention is economically advantageous and the increase in the yield is economically profitable and significant. The invention has shown that the tobacco yield can be increased by over 30% with a suitable betaine dosage, for example about 2 to 7 kg/ha. It should also be noted that even though the amount of yield increases to a considerable extent, the quality does not deteriorate. On the contrary, it has been proved here that the increase in the yield results from both a greater fresh weight and surface of the leaves, and from an earlier and more even maturation of the leaves.

According to the invention, the tobacco yield can be improved both under normal and stress conditions, which in addition to drought include for example a high salinity often connected with drought, a high temperature, etc. It should also be noted that the present invention also makes it possible to cultivate tobacco plants in areas that were previously considered unfit for cultivation, thus allowing fertile lands to be used for the cultivation of traditional nutrients, such as potato, grain, beans, etc.

The invention will be described in greater detail by means of the following examples. The examples are only provided to illustrate the invention, and they should not be considered to limit the scope of the invention in any way.

EXAMPLE 1

Two experiments were conducted during the spring and summer in order to determine the effects of different betaine concentrations on tobacco.

The experiments were conducted in the spring in Finland (60° 13' N, 24° 57' E) in the greenhouses of the University of Helsinki by utilizing the Completely Randomised Design. Forty-eight pots with a plant in each were involved in the experiment. The experiment was repeated in the summer months using the same plant material and methods as in the first experiment. The only deviation was the inducement of water stress in the second experiment three weeks earlier than in the first. Five-week old tobacco (*Nicotiana tabacum*, cv. Samsung) seedlings were transplanted into black, bottom-perforated plastic pots (475 ml, Ø 11 cm) containing vermiculite and peat in the ratio of 1:1 by volume. The pots were watered adequately until the plants were 12 weeks old, 48 cm in height and had a mean leaf number of 17. They were then subjected to water stress corresponding to a pF value of 2.9, which corresponds to about 36% soil moisture by weight in the soil medium and the meterological conditions of the greenhouse, the water stress being induced by applying 17 ml of water every 24 hours. The plants were then topped by removing the terminal buds in order to stimulate leaf expansion. Visual symptoms of leaf droop were correlated to the desired pF of 2.9 and used as the index for maintaining the status.

A fertilizer formulation of NPK 6:4:6 (Kemira Oy, Vaasa, Finland) was administered biweekly two weeks after the transplanting at the rate of 50 kg/ha until the imposition of the treatments. Insect pests were controlled with Bladafum II (Bayer) containing 11.6% of sodium chlorate as the active ingredient. Photoperiod was adjusted to 17 hours with four natrium lamps (400 W, AIRAM, Oy Airam Ab, Finland), providing a mean maximum daylight temperature of 28° C. and photosynthetically active radiation (PAR) of 434 $\mu$mol $m^2$/s. The mean night temperature was 12° C. and the relative humidity fluctuated between 42 and 45%.

A day after the water stress was induced, the plants were treated with betaine (Finnsugar Bioproducts, Finland). Two different betaine contents were used: 0.1M betaine aqueous solution (L) and 0.3M betaine aqueous solution (H). An aqueous solution (C) was control. Each plant received 20 ml of solution, with both the top and underneath of the leaves thoroughly wetted using a manually operated atomizer.

The total number of leaves per plant was recorded at harvest and the leaves were divided into green (>80% of the leaves were green) and yellow. The total leaf area ($dm^2$) per plant was also determined at harvest using a portable LI-COR planimeter (Model LI-3000, LI-COR Inc., Lincoln, Nebr., USA). The area of both green and yellow leaves was measured.

The fresh weight and the dry weight of the leaves were determined 16 days after the betaine treatment, whereupon the leaves were detached from the stem and the fresh weight was recorded by weighing (g/plant). The leaves were then dried at 50° C. for 20 hours, cooled in desiccators, and the dry weight (g/plant) and dry matter content were calculated.

The betaine content of the plants was determined 24 hours, and 4, 10 and 16 days (harvest) after the betaine application in the following manner. The five uppermost leaves were detached and washed in cold running water to dissolve and remove all adhering betaine crystals. The leaves were then dried, pulverized in liquid nitrogen, placed into cryotubes and stored in vacuum tanks containing liquid nitrogen (−196° C.) until the betaine content was determined with a HPLC method [Rajakyla and Paloposki, *J. Chromatography* 282 (1983) 595–602]

The results were analyzed statistically by means of variance analysis using the MSTAT-C program.

The fresh weight of tobacco plants increased in both experiments due to the betaine application. There was an increase of 10% in the fresh weight in Experiment I with the 0.1M betaine solution (L), whereas in Experiment II the same treatment produced a 30% increase in the fresh weight as compared with the control (C). The application of 0.3M betaine solution (H) provided 13% and 20% increases in the fresh weight over the control in Experiments I and II, respectively ($p<0.05$). The results are shown in Table 1.

TABLE 1

Effect of betaine on the fresh weight of water-stressed tobacco leaves

| Experiment | Treatment* | Mean fresh weight (g/plant) | % of the control |
|---|---|---|---|
| I | C | 68.3 | 100 |
|   | L | 75.4 | 110 |
|   | H | 76.9 | 113 |
| II | C | 38.9 | 100 |
|   | L | 50.3 | 130 |
|   | H | 46.6 | 120 |

*C = control
L = 0.1M betaine
H = 0.3M betaine
LSD = 3.70 at α-level 0.05

The significant difference between the two experiments in the fresh weight of the leaves resulted from the timing of the experiments. Experiment I was terminated 10 weeks after transplanting, when the total age of the plants was 15 weeks. Experiment II in turn was terminated 5 weeks earlier, since the water stress was imposed to coincide with the stage of rapid growth. The effects of the betaine treatment were also the greatest then.

The dry weight of tobacco leaves also increased in both experiments due to the betaine application. In Experiment I there was an increase of 8% in the dry weight with 0.1M betaine solution (L), whereas the same treatment in Experiment II produced a 32% increase in the dry weight over the control. Using the 0.3M betaine solution (H) produced 16 and 25% increases in the dry weight over the control in Experiments I and II respectively. The differences in these experiments were also due to the timing of the experiments. The results are shown in Table 2.

TABLE 2

Effect of betaine on the dry weight of water-stressed tobacco leaves

| Experiment | Treatment* | Mean dry weight (g/plant) | % of the control |
|---|---|---|---|
| I | C | 11.3 | 100 |
|   | L | 12.2 | 108 |
|   | H | 13.1 | 116 |
| II | C | 6.8 | 100 |
|   | L | 9.0 | 132 |
|   | H | 8.5 | 125 |

*C = control
L = 0.1M betaine
H = 0.3M betaine
LSD = 0.59 at α-level 0.05

There were increases of 14% and 12% in the total leaf area in Experiment I over the control with treatments L and H, whereas the same treatments in Experiment II produced 35% and 26% increases over the control. The results are shown in Table 3.

TABLE 3

Effect of betaine on the total leaf area of water-stressed tobacco leaves

| Experiment | Treatment* | Mean leaf area ($dm^2$) | % of the control |
|---|---|---|---|
| I | C | 34.4 | 100 |
|   | L | 39.1 | 114 |
|   | H | 38.6 | 112 |
| II | C | 6.9 | 100 |
|   | L | 9.3 | 135 |
|   | H | 8.7 | 126 |

*C = control
L = 0.1M betaine
H = 0.3M betaine
LSD = 0.76 at α-level 0.05

The number of green leaves in water-stressed tobacco plants at harvest decreased as a result of the betaine application. In Experiment I, there were 3% and 5% decreases in the number of green leaves at harvest due to treatments L and H, respectively. In Experiment II, treatment L produced a decrease of 5% in the number of green leaves at harvest, whereas treatment H produced a decrease of 20% in the number of green leaves. The results are shown in Table 4.

TABLE 4

Effect of betaine on the number of green leaves of water-stressed tobacco plants

| Experiment | Treatment* | Mean number of green leaves per plant | % of the control |
|---|---|---|---|
| I | C | 38.25 | 100 |
|   | L | 37.25 | 97 |
|   | H | 35.75 | 95 |
| II | C | 20.50 | 100 |
|   | L | 20.00 | 95 |
|   | H | 16.25 | 80 |

*C = control
L = 0.1M betaine
H = 0.3M betaine
LSD = 1.37 at α-level 0.05

A higher betaine content thus increased more the maturation of tobacco. Fast and even maturation is important since it reduces the number of harvests, thus reducing also the total costs.

About 13% of betaine used in all the experiments was absorbed by the leaves. In Experiment I, treatments L and H provided the absorption rates of 14% and 13%, respectively. The corresponding results in Experiment II were 12% and 11%. The proportion of absorbed betaine can be increased with a surfactant, whereupon the amount of betaine used can be correspondingly reduced. The absorption ratio was 0:1:3 for treatments C, L and H, respectively, corresponding thus entirely to the betaine concentrations used. Betaine was highly stable in the leaf tissue of the plants; after 16 days over 50% of the originally absorbed betaine was still present as determined by HPLC. The results are shown in Table 5. The decrease in the betaine content of a plant probably results from a dilution effect brought about by leaf expansion.

TABLE 5

Betaine content of water-stressed tobacco plants

| Experiment | Days after betaine treatment | Result of treatment, mean (% of fresh weight) | | |
|---|---|---|---|---|
| | | C* | L* | H* |
| I | 1 | <0.01 | 0.13 | 0.35 |
| | 4 | <0.01 | 0.13 | 0.49 |
| | 10 | <0.01 | 0.18 | 0.48 |
| | 16 | <0.01 | 0.17 | 0.47 |
| II | 1 | <0.01 | 0.22 | 0.65 |
| | 4 | <0.01 | 0.21 | 0.59 |
| | 10 | <0.01 | 0.16 | 0.44 |
| | 16 | <0.01 | 0.11 | 0.31 |

*C = control
L = 0.1M betaine
H = 6.3M betaine

The positive effect of the exogenous betaine application on the tobacco yield is clearly apparent from the results given above. In addition to increasing the fresh weight and dry weight of the leaves, as well as the leaf area, the betaine application also improved the early and even maturration of the leaves. Betaine was also found to be stable in leaf tissues, which is an indication of its ability to protect the treated plants in the long term.

EXAMPLE 2

The experiments described in Example 1 are repeated as field experiments with the betaine application rates of 3 kg/ha and 9 kg/ha. The field experiments are conducted in traditional tobacco plantations where about 50,000 plants grow per hectare. After the cultivation the tobacco leaves are gathered and weighed, and they are then dried in the air to a moisture content of about 15% and then weighed again. The yield of tobacco leaves is shown in Table 6.

TABLE 6

Effect of betaine on the yield of tobacco leaves

| Betaine (kg/ha) | Fresh yield (kg/ha) | Dry yield (kg/ha) |
|---|---|---|
| 0 (control) | 665 | 565 |
| 3 | 720 | 610 |
| 9 | 770 | 655 |

Betaine thus has a considerable effect on the yield. Utilizing a smaller dosage provides an increase of about 8% in the yield, whereas a higher dosage increases the yield as much as 16%.

We claim:

1. A method for improving the yield of tobacco plants growing under stress conditions, wherein an effective amount of betaine is exogenously applied to growing tobacco plants.

2. A method according to claim 1, wherein the stress conditions comprise high or low temperatures, drought, excess humidity or high salinity.

3. A method according to claim 2, wherein the plant grows under water stress.

4. A method according to claim 1, wherein betaine is administered together with a fertilizer or a surfactant.

5. A method according to claim 1, wherein betaine is administered once or several times during the growing season.

6. A method according to claim 5, wherein betaine is administered in a single treatment at an early stage of growth.

7. A method according to claim 1, wherein betaine is used in an amount of abour 0.2 to 40 kg/ha.

8. A method according to claim 7, wherein betaine is used in an amount of about 3 to 9 kg/ha.

* * * * *